United States Patent [19]

Loschilov et al.

[11] 4,188,952
[45] Feb. 19, 1980

[54] SURGICAL INSTRUMENT FOR ULTRASONIC SEPARATION OF BIOLOGICAL TISSUE

[76] Inventors: Vladimir I. Loschilov, ulitsa Kibalchicha, 11, kv. 83; Vadim V. Zasypkin, Uralskaya ulitsa, 6, kv. 209; Vladimir I. Petrov, Novodevichy proezd, 2, kv. 14, all of Moscow, U.S.S.R.

[21] Appl. No.: 941,796

[22] Filed: Sep. 12, 1978

Related U.S. Application Data

[63] Continuation of Ser. No. 752,972, Dec. 21, 1976, abandoned, which is a continuation of Ser. No. 617,690, Sep. 29, 1977, abandoned, which is a continuation of Ser. No. 524,308, Nov. 15, 1974, abandoned, which is a continuation of Ser. No. 429,393, Dec. 28, 1973, abandoned.

[51] Int. Cl.² .............................................. A61B 17/32
[52] U.S. Cl. .................................... 128/305; 30/144; 30/355; 128/24 A
[58] Field of Search ................. 128/305, 24 A, 317; 30/144, 272 A, 355

[56] References Cited

U.S. PATENT DOCUMENTS

| | | | |
|---|---|---|---|
| 812,507 | 2/1906 | Ludewig | 128/317 UX |
| 912,411 | 2/1909 | Putney | 30/144 |
| 2,293,286 | 8/1942 | Fenner | 30/144 |
| 2,555,735 | 6/1951 | Estabrooks | 30/355 |
| 2,685,734 | 8/1954 | Klein | 30/144 |
| 2,714,890 | 8/1955 | Vang | 128/305 |
| 2,874,470 | 2/1959 | Richards | 128/24 A X |
| 3,086,288 | 4/1963 | Balamuth et al. | 30/272 A |
| 3,433,226 | 3/1969 | Boyd | 128/305 |
| 3,636,943 | 1/1972 | Balamuth | 128/24 A |
| 3,888,004 | 6/1975 | Coleman | 30/272 A |

FOREIGN PATENT DOCUMENTS 1,391,520  1/1965  France .................................... 30/355

*Primary Examiner*—Kyle L. Howell
*Attorney, Agent, or Firm*—Holman & Stern

[57] ABSTRACT

The instrument connected to an ultrasonic oscillations source is provided with a knife to perform longitudinal mechanical oscillations at ultrasonic frequency during tissue separation. The working portion of the knife is essentially a plate made of a titanium alloy and having a pentogonal cross-section, a smooth rounding at the end thereof and two rows of teeth of triangular and wave-like shapes for separating osseous and cartilaginous tissue, respectively. A specific dimensional geometry of the instrument knife is described.

4 Claims, 7 Drawing Figures

SURGICAL INSTRUMENT FOR ULTRASONIC SEPARATION OF BIOLOGICAL TISSUE

This is a continuation of application Ser. No. 752,972, filed Dec. 21, 1976 which in turn is a Rule 60 continuation of U.S. Ser. No. 617,690 filed Sept. 29, 1977; which in turn is a Rule 60 continuation of U.S. Ser. No. 524,308, filed Nov. 15, 1974, which in turn is a Rule 60 continuation of U.S. Ser. No. 429,393, filed Dec. 28, 1973, all four now being abandoned.

The present invention relates to surgical instruments, particularly to surgical instruments for separating biological tissue and, more particularly, to such instruments using ultrasound for same.

Attempts have been made to employ an ultrasonic device in surgery for the separation of biological tissue, comprising mainly a knife connected to an ultrasonic oscillations source, performing in the course of work mechanical oscillations of ultrasonic frequency and which is brought in direct contact with the tissue being separated.

The authors of the present invention reviewed these conventional apparatus at the Third Scientific Conference on Use of Ultrasound in Traumatology, Orthopedy and Thoracal Surgery (cf. Abstracts, June 1972, Moscow).

The present invention has as its object the development and improvement of the ultrasonic separation of biological tissue and a provision for an ultrasonic surgical instrument for effecting same.

Therefore, an object of the present invention is to provide a surgical instrument for separating biological tissue capable of long service and convenient in use.

Another object of the present invention is to provide an ultrasonic surgical knife applicable in the separation of both osseous and cartilaginous tissue without applying much effort.

Yet another object of the present invention is to provide an ultrasonic surgical instrument characterized by reliable penetration into the tissue being separated and minimal thermal damage of the side surfaces of said tissue.

Still another object of the present invention is to provide a surgical knife for high-speed and a minimally traumatic separation of biological tissue that is simple in design.

These and other objects of the present invention are accomplished by a surgical instrument for ultrasonic separation of biological tissue comprising a knife performing longitudinal mechanical oscillations of ultrasonic frequency during its course of its working stroke which is brought into direct contact with the tissue to be separated, wherein, in accordance to the invention, by that the working portion of the knife which is essentially a metal plate, is smoothly rounded and which is provided with cutting teeth disposed in the zone of contact of the biological tissue to be separated.

This geometry of the cutting portion of the ultrasonic instrument provides for the most optimum cutting properties, convenience in use and versatility.

The working portion of the instrument is smoothly rounded at its end, thereby ensuring a delicate cut of the tissue during the first stage of its separation.

In accordance with one of the embodiments of the present invention the surgical instrument is characterized by the fact that the cross section of the cutting portion of the knife is of pentagonal shape so that the knife portion directly contacting the osseous tissue is thicker than the knife portion adapted to separate cartilaginous tissue, with the side faces of the knife being non-parallel with respect to each other and not contacting, during the tissue separation, the surfaces of the tissue cut.

The abovementioned pentagonal shape of the knife cross section makes it possible to avoid thermal damage of the side surfaces of the biological tissue being separated.

In accordance with another embodiment of the present invention the surgical instrument is characterized by the fact that the said teeth disposed on the cutting edge of the knife, adapted to separate the osseous tissue, are of a triangular shape and have flat edges disposed at an angle relative to the vertical line passing through the tooth top and being of a positive value.

This ensures highly effective cutting with minimal effort required.

The triangular shape of the teeth adapted to separate osseous tissue provides for their reliable penetration into the bone during the first stage of cutting, whereas the flat front edge of the tooth serves to shear off osseous tissue elements after completion of the action of its resilient and plastic properties during the displacement of the tooth for a value of the ultrasonic oscillations amplitude during the second stage of the tissue cutting process.

In accordance with another embodiment of the present invention the surgical instrument is characterized by wave-like teeth which are provided on the knife cutting edge adapted for separating cartilaginous tissue and being of a smaller thickness, said teeth being so oriented that a tangent of the supposed point of contact of the tooth with the biological tissue is parallel to the longitudinal axis of ultrasonic oscillations. Employment of the wave-like teeth provides for effective surgical separation of cartilage and reduces the force of normal pressure applied to the instrument.

This disposition of the wave-like teeth ensures a maximum value for the cutting force vector in the direction of the main movement, with the normal pressure applied to the instrument being optimum.

In accordance with another embodiment of the present invention the surgical instrument is characterized by the fact that one edge of the knife, that is comparatively wide, is provided with triangular teeth, and the other edge thereof, which is comparatively narrow, is provided with teeth having a wave-like shape.

This embodiment of the knife makes it possible to provide an ultrasonic instrument of a universal designation for separating by one and the same instrument biological tissue varying in type and density.

The combination of the two types of cuts provided on one and the same working element of the ultrasonic cutting instrument is due to the character of the skeleton part being separated in the course of the operation.

When separating, for instance a sternum that has both osseous and cartilaginous tissue, employment of the combined ultrasonic cutting instrument makes it possible to reduce the time for the bone cutting and makes it convenient for the surgeon to perform the latter procedure.

In accordance with another embodiment of the present invention the surgical instrument is characterized by the fact that the thickness for cutting a comparatively wider edge is from 0.6–2 mm, the pitch and height of the teeth constitute approximately 0.8–1 mm, whereas the front angle of the tooth is about 0°±10° relative to the vertical line passing through the tooth top, with angle of the tooth proper constituting 35°-40°.

The pitch between the teeth and the height of the latter are determined by the optimum ratio between the cutting force and the force of normal pressure, as well as the delicate operation of the instrument.

As it has already been stated above, employment of negative front angles (the angles between the teeth and biological tissue) with respect to the direction of propagation of ultrasonic oscillations, provides for the greatest possible efficiency of the process.

However, the use of teeth whose angles have great values results in the reduction of the tooth strength and an increase in the cutting edge wear.

This is one of the optimum specific variants of the embodiment of the ultrasonic knife cutting portion.

The surgical knife is also characterized by the fact that the comparatively narrow edge is extremely sharp, the teeth pitch is 4.5-5 mm and the radius of curvature of each wavelike tooth is about 1.5-2 mm.

The above-given geometry is essentially one of the optimum specific dimensional variants of the embodiment of the ultrasonic instrument having a knife with wave-like teeth.

With the pitch exceeding 5 mm and the radius varying by less than 1.5 mm, the tooth deeply penetrates into the tissue, whereby the force of the cutting process increases and the latter becomes very much similar to that of the ultrasonic cutting of cartilage by a saw, which results in a smaller amplitude of oscillations, a lower efficiency of the process and a higher temperature in the cutting zone.

With the pitch being smaller than 4.5 mm and the radius increasing by over 2 mm, the effect of the pressure concentration in the zone of the tooth—biological tissue contact decreases, thereby resulting in a greater force of pressure being applied to the instrument and a drop in the amplitude of oscillations.

Besides, the surgical instrument is characterized by the fact that the knife is made from a titanium alloy and, with the length of its cutting portion being 23-25 mm, the width—4-5 mm, and the curvature radius of the cutting portion and constitutes approximately 12-16 mm.

Titanium alloys are the most optimum material for manufacturing an ultrasonic medical cutting instrument.

They possess good acoustic and anti-corrosion properties, exhibit a small specific weight, and allow for the instrument to be used when the amplitudes of oscillations are rather great.

The length of the cutting portion was determined by the condition that the instrument has no bending oscillations taking place therein and is durable.

The following detailed description of an exemplary embodiment of the present invention is given with reference to the accompanying drawings, in which.

Figure 1:
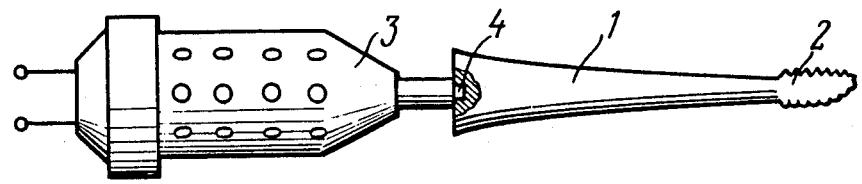
FIG. 1 shows an acoustic head with a changeable ultrasonic instrument, according to the invention.

The present invention relates, inter alia, to the design of the working portion of an ultrasonic cutting instrument. The ultrasonic instrument is designed for the separation of tight (osseous and cartilaginous) biological tissue. The ultrasonic cutting instrument (FIG. 1) is essentially a titanium rod 1 whose cross section changes in conformity with the exponential law and which has a working portion—cutting instrument 2 disposed at the end thereof, with the instrument being an integral part of the acoustic system. It is fixed to an acoustic head 3 with the aid of a thread joint 4 and is changeable. The ultrasonic cutting instrument is a part of the medical apparatus adapted for ultrasonic cutting, welding and deposition of biological tissue.

Figure 2:
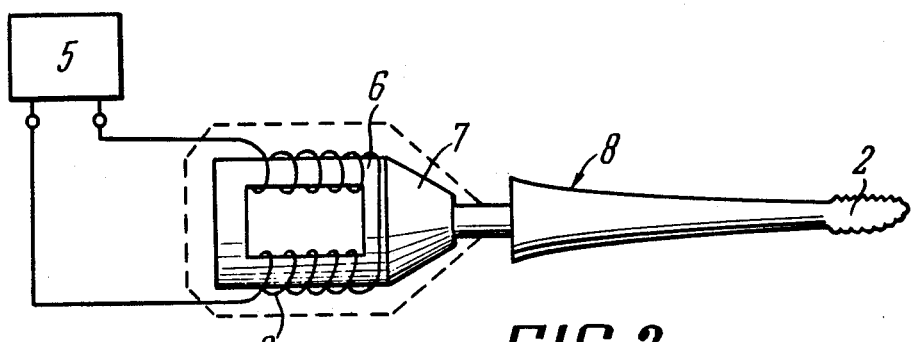
FIG. 2 shows a surgical instrument for separating biological tissue and schematically shows the acoustic system of the apparatus.

The apparatus comprises a 250 Wt. ultrasonic generator 5 (FIG. 2), three acoustic heads (for welding, deposition and cutting) and a set of instruments for ultrasonic treatment of biological tissue.

The apparatus also comprises a sealed box (not shown in the drawings) for sterilization of acoustic heads and instruments.

The acoustic system (FIG. 2) of the apparatus comprises a generator 5 of electric oscillations, a magnetostriction converter 6, a conical half-wave concentrator 7 in the form of a cylinder and a changeable half-wave concentrator instrument 8. The system operates under resonance conditions. The magnetostriction converter 6 is fixedly connected to the conical-cylindrical concentrator 7, and is an integral part of the acoustic head. The converter 6 is assembled of nickel plates that are fused together, and has an excitation winding 9.

Figure 3:
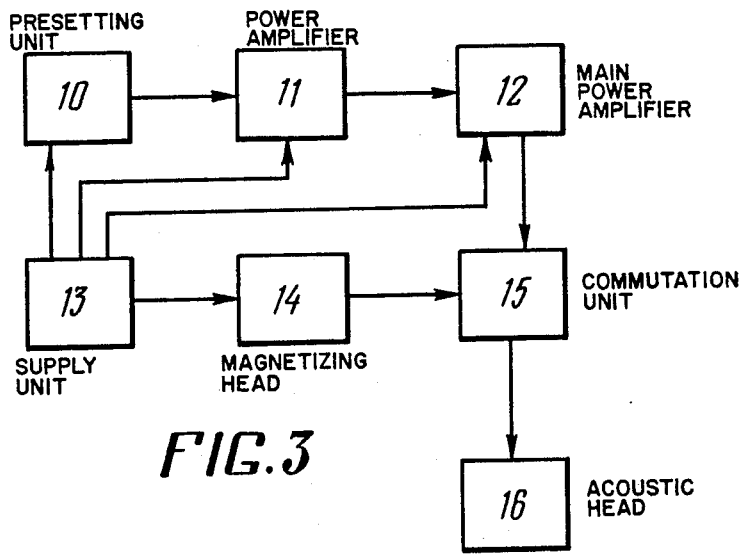
FIG. 3 shows a block diagram of the generator of the instrument for ultrasonic separation of biological tissue.

The ultrasonic generator 5 whose block diagram is shown in FIG. 3 comprises a presetting generator 10, a power amplifier 11, a main power amplifier 12, a supply unit 13, a magnetizing unit 14 and a commutation unit 15. Connected to the output of the ultrasonic generator is an acoustic head 16 having the instrument-concentrator. The ultrasonic generator 5 (FIG. 2) is supplied from A.C., 220 W, 50 Hz mains. The power consumed does not exceed 0.45 kWt, the rated power of the generator being 250 W, and the working frequency—26.5 kHz. The apparatus operates as follows.

The acoustic head 3 (FIG. 1) having the ultrasonic, for instance, cutting instrument 2 fixed thereon is connected with the aid of a plug connector to the outlet of the ultrasonic generator 5 that is switched over by means of a tumbler (not shown in the drawings).

With the tumbler in the "mains" position, the ultrasonic generator 5 (FIG. 2) starts generating alternating current at an ultrasonic frequency.

The A.C. is supplied to the winding 9 of the magnetostriction converter which converts electric oscillations into mechanical ones of ultrasonic frequency. The mechanical oscillations thus obtained are amplified by the conical-cylindrical concentrator 7 and the changeable concentrator—instrument 8, and are imparted to the working portion 2 which effects separation of biological tissue. While holding the acoustic head with the instrument and displacing the working portion over the surface, the surgeon separates the tissue, the amplitude of oscillations of the working portion being as high as 60 microns. The ultrasonic separation possesses a number of advantages over the conventional separation of biological tissue, the main ones residing in the following:

little damage of the tissue, decreased efforts applied when cutting, hemostatic (blood-stopping) effect. The smaller the efforts applied by the surgeon to the ultrasonic cutting instrument, the higher the efficiency of the cutting process.

Figures 4, 5:
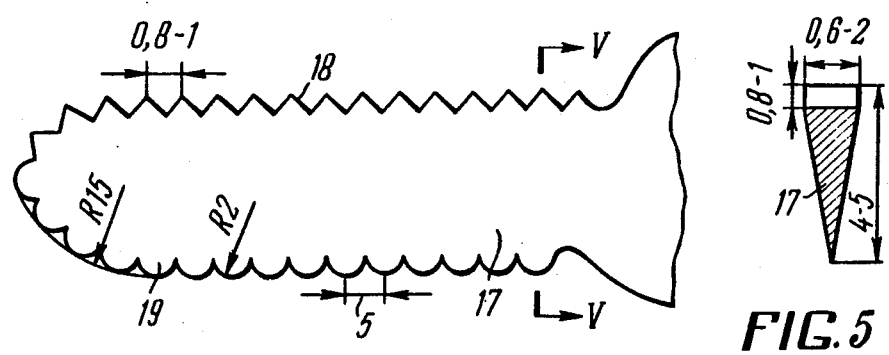
FIG. 4 shows the working portion of an ultrasonic cutting instrument, according to the present invention.
FIG. 5 shows a cross section of the working portion of the instrument shown in FIG. 4.

The working portion 2 of the ultrasonic cutting instrument with which the surgeon directly performs the separation of biological tissue is essentially a plate 17 (FIG. 4) the cross-section of its working portion being of pentagonal shape (FIG. 5); the wider cutting edge of the plate 17 is provided with teeth 18 of a triangular shape to separate osseous tissue, and the opposite narrow cutting edge is provided with wave-like teeth 19 to separate cartilaginous tissue. In the course of operation the working portion of the instrument gets hot, and the high temperatures may result in necrosis of the live cells of the tissue.

The pentagonal shape of the profile of the ultrasonic cutting instrument ensures minimal thermal damage to the side surfaces of the tissue being cut owing to a smaller area of contact of the instrument with the biological tissue.

The end portion of the instrument working portion is smoothly rounded, thereby providing for delicate cutting of the tissue during the first state of its separation.

Figures 6, 7:
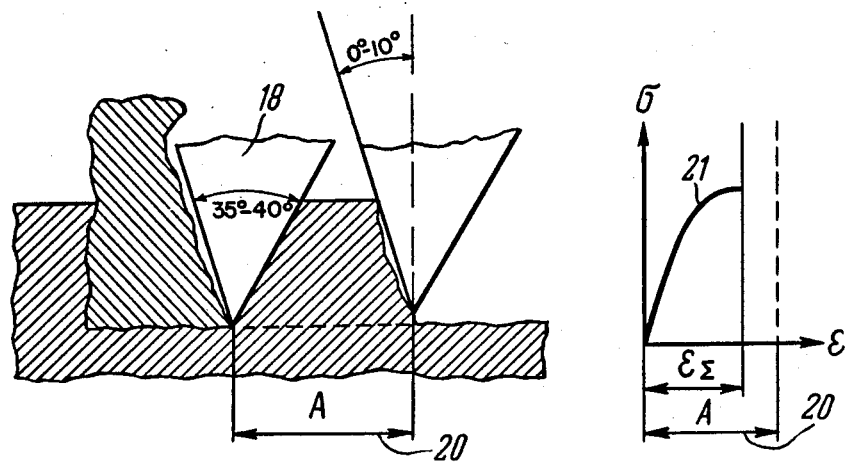
FIG. 6 shows a diagram illustrating the mechanism of ultrasonic separation of osseous tissue.
FIG. 7 shows a diagram of the deformation characteristic during separation of osseous tissue.

The triangular shape of the teeth for separating osseous tissue ensures their reliable penetration into the bone during the stage of the cutting process, while the flat front edge of the tooth serves to shear off the osseous tissue element after completion of the action of its resilient and plastic properties during displacement of the tooth 18 (FIG. 6) over the amplitude value of 20 ultrasonic oscillations during the second stage of the tissue cutting process. FIG. 7 shows deformation characteristic 21 during separation of osseous tissue, wherein $\sigma$—applied mechanical loading;
$\epsilon$—deformation value of osseous tissue.

The triangular teeth 18 for separating osseous tissue are oriented in such a manner that the angle between the front edge of the tooth and the vertical line passing through the tooth top is of a positive value. Employment of these angles brings about higher efficiency of the cutting process and lower temperatures in the cutting zone.

In the case of the separation of cartilaginous tissue by means of an ultrasonic instrument the optimum cutting process is the one residing in the intersection of cartilaginous fibres by an instrument of a scalpel type.

Due to this, the cutting edge used for the separation of cartilaginous tissue is made extremely sharp.

From the viewpoint of its density, cartilage is in between osseous and flesh tissue, and, therefore, separation of the cartilaginous tissue by an instrument of a scalpel type will result in an extreme increase in the force of normal pressure applied by the surgeon to the instrument.

The use of the wave-like teeth makes it possible to raise the efficiency of the process of cartilage ultrasonic cutting and to decrease the force of normal pressure on the instrument by way of increasing the specific pressure in the zone of contact between the tooth and biological tissue, thereby decreasing the contact area.

It should be noted that the wave-like teeth 19 are so arranged that a tangent to the tooth at the supposed point of its contact with the tissue is parallel to the axis of propagation of ultrasonic oscillations. This arrangement of the wave-like teeth provides for a maximal value of the vector of the cutting force in the direction of the main movement at a preset optimum value of the force of normal pressure on the instrument.

The combination of the two types of; teeth 19 and 18 provided on one and the same working portion 17 of the ultrasonic cutting tool is determined by the character of the skeleton part to be separated during the operation.

When separating, for instance, a sternum that has both osseous and cartilaginous tissue, the employment of the combined ultrasonic cutting instrument makes it possible to reduce the time of cutting the bone and makes it convenient for the surgeon to perform the process itself.

The wider cutting edge is made 0.6–2 mm thick (FIG. 5) to ensure long service of the instrument and to decrease damage of the bone.

The abovementioned height of the teeth is chosen in order to maintain a sufficient value of the "net"-section (1 mm), as well as to prevent clogging of the teeth with bone chips.

The pitch between the teeth is determined by the optimum ratio between the cutting force $P_X$ and the force $P_Y$ of normal pressure, as well as the delicate mode of operation of the instrument.

As it has already been said, employment of the negative front angles (the angles between the tooth and biological tissue) relative to the direction of the propagation of the ultrasonic oscillations provides for the greatest efficiency of the process.

However, the use of teeth having high angle values results in a reduced strength of the tooth and a greater wear-out time for the cutting edge.

Since the structure of the cartilaginous tissue is of a fibrous character, the optimum process of ultrasonic separation of cartilage is that of the intersection of cartilaginous fibres rather than shearing off. In order to carry out the process, the cutting edge is made extremely sharp.

As has already been stated above, the wave-like projections allow for a decrease the force $P_Y$ and to raises the efficiency of the cutting process.

The radius of curvature and the pitch of the teeth have been found experimentally.

When the pitch exceeds 5 mm and the radius is changed by less than 1.5 mm, the tooth deeply penetrates into the tissue, the cutting force $P_Z$ increases, and the process becomes very much similar to that of ultrasonic cutting of cartilage with the aid of a saw, which brings about a drop in the oscillations amplitude, a lower efficiency of the process and higher temperatures in the zone of cutting.

When the pitch is decreased by less than 4.5 mm and the radius of tooth projections are increased by more than 2 mm, the effect of concentration of pressure in the zone of contact between the tooth and the biological tissue diminishes, thereby resulting in a greater force of pressure acting on the instrument and a drop in the oscillations amplitude.

Titanium alloys are the most optimum material for the ultrasonic medical cutting instrument.

Titanium alloys possess good acoustic properties, anti-corrosion properties and exhibit a small specific weight, and allows the instrument to be used when the amplitudes of oscillations are rather great.

The length of the cutting portion was chosen so as to avoid overbending oscillations in the instrument and to ensure long service.

In some cases, for example when performing oncological operations, the bending oscillations of the instrument are useful, as they cause a temperature rise in the zone of cutting.

What we claim is:

1. A surgical instrument for the ultrasonic separation of biological tissue comprising a cutting means having a longitudinally extending axis, opposite end portions, and a pentagonal cross-section, said pentagonal cross-section defining a rectangular first portion attached to a triangular second portion; and an ultrasonic oscillation means secured to said cutting means at one end portion thereof providing longitudinal mechanical oscillations of said cutting means in the direction of said axis at an ultrasonic frequency, the other end portion of said cutting means being rounded having a curvature radius, said first portion of said cutting means having triangular-shaped teeth for cutting osseous tissue and said second portion of said cutting means having arch-like shaped teeth for cutting cartilaginous tissue; said triangular-shaped teeth having front edges and back edges, said front edges being the edge of each tooth closest to said rounded end portion of said cutting means, said back edge being the edge of each tooth closest to said end portion of said cutting means secured to said ultrasonic oscillations means; a first angle defined between said front edge of each tooth and a vertical line passing through the tooth perpendicular to said axis; a second angle defined between said front edge and said back edge of each tooth; a height; and a pitch; said front edge is flat and said first angle has a positive value of from 0° to 10°, said pitch is from 0.9 to 1.0 mm, and said second angle is from 35° to 40°.

2. The surgical instrument of claim 1 wherein said arch-like shaped teeth have a pitch, and each tooth has a radius of curvature, each tooth being oriented such that a tangent to the supposed point of contact of said tooth to the tissue is parallel to said axis.

3. The surgical instrument of claim 2 wherein said pitch of said arch-like shaped teeth is from 4.5 to 5.0 mm, and said radius of curvature of each tooth is from 1.5 to 2.0 mm.

4. The surgical instrument of claim 1 wherein said cutting means is made of titanium and has an overall length of from 23 to 25 mm, an overall height between said portion and said second portion of from 4 to 5 mm, and said curvature radius of said rounded end portion is from 12 to 16 mm.

* * * * *